United States Patent
Mcdonald (10) Patent No.: US 8,209,017 B1
(45) Date of Patent: Jun. 26, 2012

(54) SEPTUM FOR COVERING A FASTENER ASSEMBLY ON A CONNECTOR OF AN IMPLANTABLE ELECTRIC STIMULATION SYSTEM AND METHODS OF MAKING AND USING

(75) Inventor: Matthew Lee Mcdonald, Pasadena, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 832 days.

(21) Appl. No.: 12/104,241

(22) Filed: Apr. 16, 2008

(51) Int. Cl.
*A61N 1/375* (2006.01)

(52) U.S. Cl. ............ 607/37; 411/377; 411/360; 607/36

(58) Field of Classification Search ............ 607/36, 607/37; 439/814; 411/393, 377, 360, 372–373, 411/999; 403/362; 128/419, 784
See application file for complete search history.

(56) References Cited

U.S. PATENT DOCUMENTS

| | | | |
|---|---|---|---|
| 3,908,668 A * | 9/1975 | Bolduc | ............ 607/37 |
| 4,485,268 A | 11/1984 | Kaplan | |
| 4,633,889 A | 1/1987 | Talalla et al. | |
| 5,000,177 A * | 3/1991 | Hoffmann et al. | ............ 607/2 |
| 5,383,914 A | 1/1995 | O'Phelan | |
| 5,509,928 A * | 4/1996 | Acken | ............ 607/37 |
| 5,545,188 A | 8/1996 | Bradshaw et al. | |
| 5,873,368 A | 2/1999 | Sabin et al. | |
| 6,181,969 B1 | 1/2001 | Gord | |
| 6,516,227 B1 | 2/2003 | Meadows et al. | |
| 6,597,953 B2 | 7/2003 | Boling | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 7,004,948 B1 | 2/2006 | Pianca et al. | |
| 7,044,942 B2 | 5/2006 | Jolly et al. | |
| 7,244,150 B1 | 7/2007 | Brase et al. | |
| 2002/0116042 A1 | 8/2002 | Boling | |
| 2003/0040780 A1* | 2/2003 | Haeg et al. | ............ 607/36 |

(Continued)

FOREIGN PATENT DOCUMENTS

EP          0569839 B1       4/1997

(Continued)

OTHER PUBLICATIONS

U.S. Appl. No. 10/353,101, filed Jan. 27, 2003.

(Continued)

*Primary Examiner* — Kennedy J. Schaetzle
*Assistant Examiner* — Erica Lee
(74) *Attorney, Agent, or Firm* — Frommer Lawrence & Haug LLP; Bruce E. Black (57) ABSTRACT

A connector for an electrostimulation lead includes a connector housing defining a fastener aperture, a septum disposed over the fastener aperture, and a fastener for mating with the fastener aperture to secure a received lead to the connector housing so that at least one terminal disposed on the received lead electrically couples with at least one conductor contact disposed in the connector housing. The septum includes a septum flap and an attachment cuff. The septum flap is configured and arranged for extending over the fastener aperture and for receiving a tool for folding the septum flap open to expose the fastener aperture. The attachment cuff is configured and arranged for coupling the septum flap to the connector housing. The fastener is configured and arranged to be disposed in the fastener aperture and to be tightened against the lead to hold the lead within the connector housing.

19 Claims, 9 Drawing Sheets

U.S. PATENT DOCUMENTS

| | | |
|---|---|---|
| 2004/0059392 A1 | 3/2004 | Parramon et al. |
| 2005/0165465 A1 | 7/2005 | Pianca et al. |
| 2007/0255365 A1 | 11/2007 | Gerber et al. |
| 2008/0063490 A1 | 3/2008 | Fruland et al. |
| 2008/0183241 A1 | 7/2008 | Bedenbaugh |
| 2008/0262564 A1 * | 10/2008 | Alexander et al. .............. 607/37 |

FOREIGN PATENT DOCUMENTS

| | | |
|---|---|---|
| EP | 0805648 B1 | 5/2000 |
| WO | 96/22727 A1 | 8/1996 |
| WO | 03/063951 A1 | 8/2003 |
| WO | 2008/016929 A2 | 2/2008 |

OTHER PUBLICATIONS

U.S. Appl. No. 10/503,281, filed Mar. 11, 2005.
U.S. Appl. No. 11/238,240, filed Sep. 29, 2005.
U.S. Appl. No. 11/319,291, filed Dec. 27, 2005.
U.S. Appl. No. 11/327,880, filed Jan. 9, 2006.
U.S. Appl. No. 11/396,309, filed Mar. 31, 2006.
U.S. Appl. No. 11/375,638, filed Mar. 14, 2006.
U.S. Appl. No. 11/393,991, filed Mar. 30, 2006.
U.S. Appl. No. 11/532,844, filed Sep. 18, 2006.

* cited by examiner

SEPTUM FOR COVERING A FASTENER ASSEMBLY ON A CONNECTOR OF AN IMPLANTABLE ELECTRIC STIMULATION SYSTEM AND METHODS OF MAKING AND USING

TECHNICAL FIELD

The present invention is directed to the area of implantable electrical stimulation systems and methods of making and using the systems. The present invention is also directed to implantable electrical stimulation systems that include a septum covering a fastener assembly disposed on a connector coupling two or more implanted components of an electrical stimulation system, as well as methods of making and using the connectors, septa, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Moreover, electrical stimulation systems can be implanted subcutaneously to stimulate subcutaneous tissue including subcutaneous nerves such as the occipital nerve.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a connector for receiving an electro-stimulation lead includes a connector housing, a plurality of connector contacts, a septum, and a fastener. The connector housing defines an opening for receiving a proximal end of the lead. The connector housing also includes a fastener aperture configured and arranged for receiving the fastener for securing the received lead in the connector housing. The plurality of connector contacts are disposed in the connector housing and are configured and arranged to couple to at least one terminal disposed on the proximal end of the lead. The septum is disposed on the connector housing. The septum includes a proximal end and a distal end and includes a septum flap and an attachment cuff. The septum flap is configured and arranged for extending over the fastener aperture and for receiving a tool for folding the septum flap open to expose the fastener aperture. The attachment cuff is configured and arranged for coupling the septum flap to the connector housing. The proximal end of the septum flap is attached to the proximal end of the attachment cuff and the distal end of the septum flap overhangs the distal end of the attachment cuff to receive the tool for folding the septum flap open. The fastener is configured and arranged to be disposed in the fastener aperture and to be tightened against the lead to hold the lead within the connector housing.

In another embodiment, an electrical stimulating system includes a lead, a control module, and a connector. The lead has a proximal end and a distal end and includes a plurality of electrodes disposed on the distal end of the lead, a plurality of terminals disposed on the proximal end of the lead, and a plurality of conductor wires extending along the lead to couple the electrodes electrically to the terminals. The control module is configured and arranged to electrically couple to the lead. The control module includes a housing, and an electronic subassembly disposed in the housing. The connector is configured and arranged for receiving the lead. The connector includes a connector housing, a plurality of connector contacts, a septum, and a fastener. The connector housing defines an opening for receiving a proximal end of the lead. The connector housing also includes a fastener aperture configured and arranged for receiving a fastener for securing the received lead in the connector housing. The plurality of connector contacts are disposed in the connector housing and are configured and arranged to couple to at least one terminal disposed on the proximal end of the lead. The septum is disposed on the connector housing. The septum includes a proximal end and a distal end and includes a septum flap and an attachment cuff. The septum flap is configured and arranged for extending over the fastener aperture and for receiving a tool for folding the septum flap open to expose the fastener aperture. The attachment cuff is configured and arranged for coupling the septum flap to the connector housing. The proximal end of the septum flap is attached to the proximal end of the attachment cuff and the distal end of the septum flap overhangs the distal end of the attachment cuff to receive the tool for folding the septum flap open. The fastener is configured and arranged to be disposed in the fastener aperture and to be tightened against the lead to hold the lead within the connector housing.

In yet another embodiment, a method for stimulating patient tissue includes implanting a lead into a patient, disposing a proximal end of the lead into a connector electrically coupled to a control module, and providing electrical signals from the control module to electrically stimulate patient tissue using at least one of a plurality of electrodes disposed on a distal end of the lead. The plurality of electrodes are electrically coupled to at least one terminal disposed on the proximal end of the lead. The connector includes at least one connective contact that electrically couples to at least one of the terminals of the lead. The connector also includes a fastener aperture and a septum. The fastener aperture is configured and arranged for receiving a fastener for securing the lead to the connector. The septum is disposed on the connector and extends over the fastener aperture. The septum includes an attachment cuff and a septum flap. The attachment cuff is configured and arranged for coupling to the connector. The septum flap is coupled to the attachment cuff and configured and arranged for receiving a tool to fold back the septum flap to facilitate access to the fastener.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation systems that include a septum covering a fastener assembly disposed on a connector coupling two or more implanted components of an electrical stimulation system, as well as methods of making and using the connectors, septa, and electrical stimulation systems.

Suitable implantable electrical stimulation systems include, but are not limited to, an electrode lead ("lead") with one or more electrodes disposed on a distal end of the lead and one or more terminals disposed on a proximal end of the lead. Leads include, for example, percutaneous leads, paddle leads, and cuff leads. Examples of electrical stimulation systems with leads are found in, for example, U.S. Pat. Nos. 6,181, 969; 6,516,227; 6,609,029; 6,609,032; and 6,741,892; and U.S. patent application Ser. Nos. 10/353,101, 10/503,281, 11/238,240; 11/319,291; 11/327,880; 11/375,638; 11/393, 991; and 11/396,309, all of which are incorporated by reference.

Figure 1:
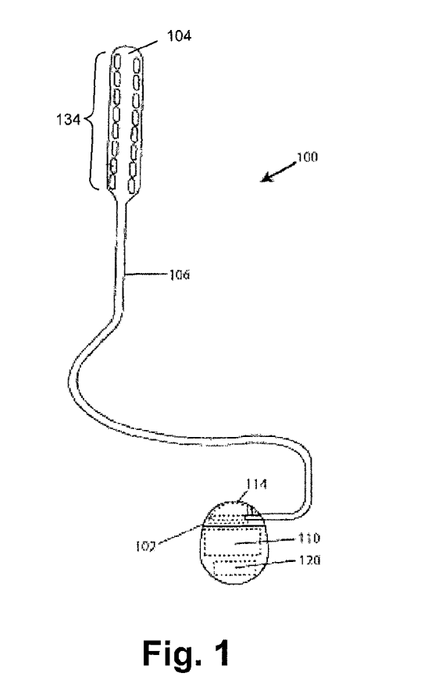
FIG. 1 is a schematic view of one embodiment of an electrical stimulation system, according to the invention.
Figure 2:
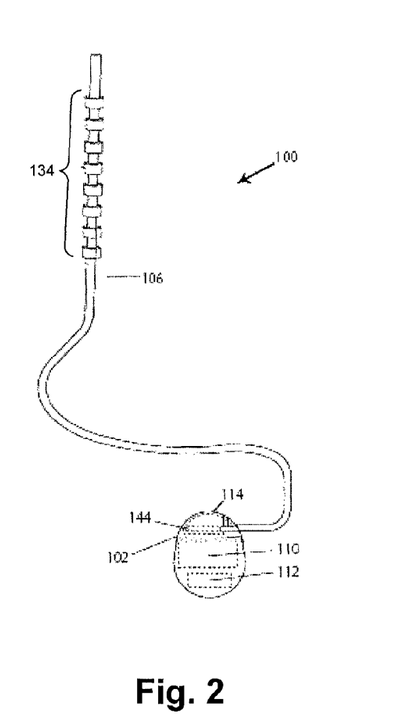
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the lead body 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (see FIGS. 2, and 3A-3B) into which the proximal end of the lead body 106 can be plugged to make an electrical connection via conductive contacts on the control module 102 and terminals on the lead body 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the lead body 106 and the control module 102 to extend the distance between the lead body 106 and the control module 102 of the embodiments shown in FIGS. 1 and 2.

The electrical stimulation system or components of the electrical stimulation system, including one or more of the lead body 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or lead body 106 are typically disposed in, or separated by, a non-conductive, biocompatible material such as, for example, silicone, polyurethane, polyetheretherketone ("PEEK"), epoxy, and the like or combinations thereof. The paddle body 104 and lead body 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end. The non-conductive, biocompatible material of the paddle body 104 and the lead body 106 may be the same or different. The paddle body 104 and the lead body 106 may be a unitary structure or can be formed as two separate structures that are permanently or detachably coupled together.

Terminals (e.g., 310 in FIG. 3A and 330 of FIG. 3B) are typically disposed at the proximal end of the lead for connection to corresponding conductive contacts (e.g., 314 in FIG. 3A and 344 of FIG. 3B) in the control module 102 (or to conductive contacts on a lead extension). Conductor wires (not shown) extend from the terminals (e.g., 310 in FIG. 3A and 330 of FIG. 3B) to the electrodes 134. Typically, one or more electrodes 134 are electrically coupled to a terminal (e.g., 310 in FIG. 3A and 330 of FIG. 3B). In at least some embodiments, each terminal (e.g., 310 in FIG. 3A and 330 of FIG. 3B) is only connected to one electrode 134. The conductor wires may be embedded in the non-conductive material of the lead or can be disposed in one or more lumens extending along the lead. In some embodiments, there is an individual lumen for each conductor wire. In other embodiments, two or more conductor wires may extend through a lumen. There may also be one or more lumens that open at, or near, the proximal end of the lead, for example, for inserting a stylet rod to facilitate placement of the lead within a body of a patient. Additionally, there may also be one or more lumens that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
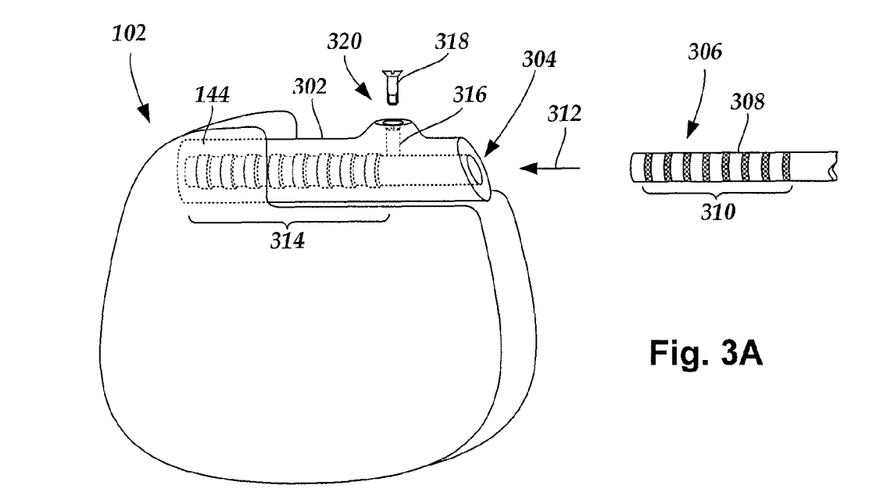
FIG. 3A is a schematic view of one embodiment of a proximal portion of a lead and a control module of an electrical stimulation system, according to the invention.
Figure 3B:
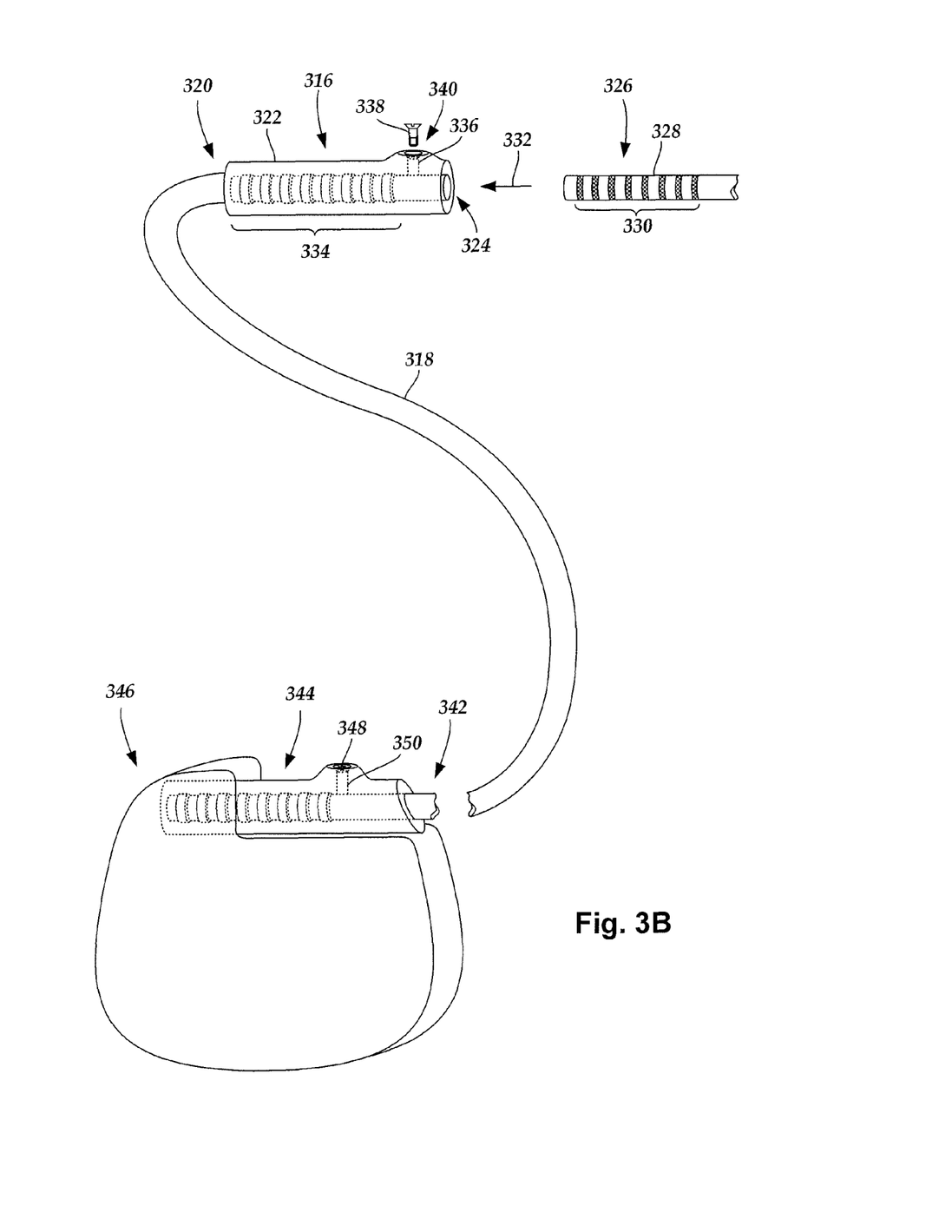
FIG. 3B is a schematic view of one embodiment of a proximal portion of a lead and a lead extension for an electrical stimulation system, according to the invention.

Fastener assemblies are sometimes used to secure two or more coupled components of an electrical stimulation system. For example, a fastening assembly may be used to secure a lead (or lead extension) coupled to a connector disposed as part of a control module (as shown in FIG. 3A) or a lead extension (as shown in FIG. 3B). In FIG. 3A, the connector 144 is disposed as part of the control module 102. The connector 144 includes a connector housing 302 that is optionally part of the housing of the control module. The connector housing 302 defines an opening 304 into which a proximal end 306 of a lead 308 with terminals 310 can be inserted, as shown by directional arrow 312. The connector housing 302 also includes a plurality of conductive contacts 314 and a fastener aperture 316. When the lead 308 is inserted into the opening 304, the conductive contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. No. 7,244,150 and U.S. patent application Ser. No. 11/532,844, which are incorporated by reference.

A fastener 318 can be mated with the fastener aperture 316 to form a fastener assembly 320. The fastener assembly 320 can be used to secure the lead 308 to the control module 102. Fasteners and fastener apertures can be made from many different metallic or ceramic materials suitable for implantation. In FIG. 3A, the fastener 318 is shown as a set screw. However, other types of fasteners may be used as well, such as pins, posts, and the like or combinations thereof. The fastener aperture 316 may be positioned in any location along the length of connector 144. In FIG. 3A and in subsequent figures, fastener apertures are shown disposed in proximity to the opening 304 of the connector for clarity of illustration.

In FIG. 3B, a connector 316 is disposed on a lead extension 318. The connector 316 is shown disposed at a distal end 320 of the lead extension 318. The connector 316 includes a connector housing 322. The connector housing 322 defines an opening 324 into which the proximal end 326 of the lead 328 with terminals 330 can be inserted, as shown by directional arrow 332. The connector housing 322 also includes a plurality of conductive contacts 334 and a fastener aperture 336. When the lead 328 is inserted into the opening 324, the conductive contacts 334 disposed in the connector housing 322 can be aligned with the terminals 330 on the lead 328 to electrically couple the lead extension 318 to the electrodes (134 of FIG. 1) disposed at a distal end of the lead 328. A fastener 338 can be mated with the fastener aperture 336 to form a fastener assembly 340, which can be used to secure the lead 328 to the lead extension 318.

In at least some embodiments, the proximal end of a lead extension is similarly configured and arranged as a proximal end of a lead. The lead extension 318 may include a plurality of conductive wires (not shown) that electrically couple the conductive contacts 334 to a proximal end 342 of the lead extension 318 that is opposite to the distal end 320. In at least some embodiments, the conductive wires disposed in the lead extension 318 can be electrically coupled to a plurality of terminals (not shown) disposed on the proximal end 342 of the lead extension 318. In at least some embodiments, the proximal end 342 of the lead extension 318 is configured and arranged for insertion into a connector disposed in another lead extension. In other embodiments, the proximal end 342 of the lead extension 318 is configured and arranged for insertion into a connector disposed in a control module. As an example, in FIG. 3B the proximal end 342 of the lead extension 318 is inserted into a connector 344 disposed in a control module 346. A fastener 348 is disposed in a fastener aperture 350 to secure the proximal end 342 of the lead extension 318 to the control module 342.

Direct exposure to bodily fluids or tissues may cause damage to a fastener assembly disposed on a connector. Bodily fluids or tissues may corrode of one or more components of a fastener assembly, or may cause a fastener to become stuck in a fastener aperture. Additionally, when a conductive fastener is used as an active electrical element, interactions with bodily fluids or tissues may create additional electrical current pathways that may cause improper performance or failure of the electrical stimulation system which might even result in harm to a patient.

Figure 4A:
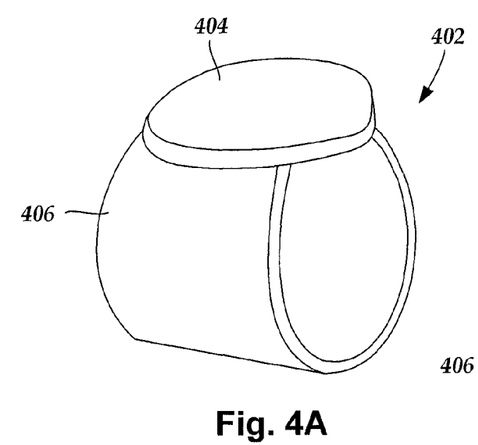
FIG. 4A is a schematic perspective view of one embodiment of a septum, according to the invention.

Shielding implanted fastener assemblies from bodily fluids or tissues can provide some degree of protection. One way to shield a fastener assembly from bodily fluids or tissues is to cover the fastener assembly with a septum. In some embodiments, a septum is integrally molded as part of a connector housing. In other embodiments, a septum is either removably or permanently disposed over a connector housing. FIG. 4A is a schematic perspective view of one embodiment of a septum 402. The septum 402 includes a septum flap 404 and an attachment cuff 406. The attachment cuff 406 is configured and arranged to be disposed on a connector housing. It will be understood that in some embodiments the attachment cuff may be part of the housing. The septum flap 404 is configured and arranged to cover a fastener aperture on a connector (see FIG. 3A and FIG. 3B). The septum 402 can be manufactured using any elastomeric, non-conductive materials suitable for implantation, including, but not limited to, silicone, urethane, silicone-urethane copolymers, and the like or combinations thereof. The septum 402 may be formed in the desired shape by any process including, for example, molding (including injection molding), casting, and the like.

In at least some embodiments, one or more reinforcing components may be added to the septum flap 404 to increase the durability of the septum flap 404 and also to decrease the likelihood of the septum flap 404 being damaged (e.g., punctured by a tool) which may potentially result in an inability of the septum flap 404 to form an interference fit or to impede the flow of fluid. In at least some embodiments, the one or more reinforcing components are completely encapsulated by the material of the septum flap 404. In other embodiments, the reinforcing component may be exposed on at least one surface. Many different types of reinforcing components can added to the septum flap 404 including, for example, woven or knitted meshes, plastic sheets, molded components, metallic components, and the like or combinations thereof. In at least some embodiments, when the reinforcing component(s) includes an electrically-conductive material, the electrically-conductive material may, at most, pass through one side of the septum flap 404.

Figure 4B:
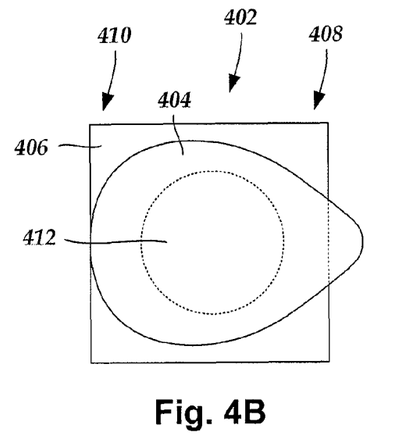
FIG. 4B is a schematic top view of one embodiment of a septum, according to the invention.

FIG. 4B is a schematic top view of the septum 402. The septum 402 includes a distal end 408 and a proximal end 410. The distal end 408 of the septum flap 404 overhangs the distal end 408 of the attachment cuff 406 and can be used to facilitate opening of the septum flap 404. The attachment cuff 406 defines an access aperture 412 extending through the attachment cuff 406 and disposed beneath the septum flap 404. In FIG. 4B, the access aperture 412 is shown as a circular dotted line. The size and shape of the access aperture 412 can vary. In some embodiments, the access aperture 412 is approximately the same size and shape as a head of a fastener (see FIG. 3A and FIG. 3B). In other embodiments, the access aperture 412 is approximately the same size and shape as the septum flap 404 (not including the overhanging portion of the distal end). As will be seen, many different sizes and shapes can be used for the access aperture 412, so long as the access aperture 412 is large enough that a fastener and a tool can be passed through the access aperture 412 and not larger than the overlying septum flap 404. In at least some embodiments, the septum 402 is formed as a single component, with the proximal end 410 of the septum flap 404 attached to a portion of the proximal end 410 of the attachment cuff 406 in proximity to the access aperture 412. In other embodiments, the septum flap 404 and the attachment cuff 406 are formed separately and the proximal end 410 of the septum flap 404 is permanently attached to a portion of the proximal end 410 of the attachment cuff 406 in proximity to the access aperture 412 subsequent to manufacture.

Figure 5A:
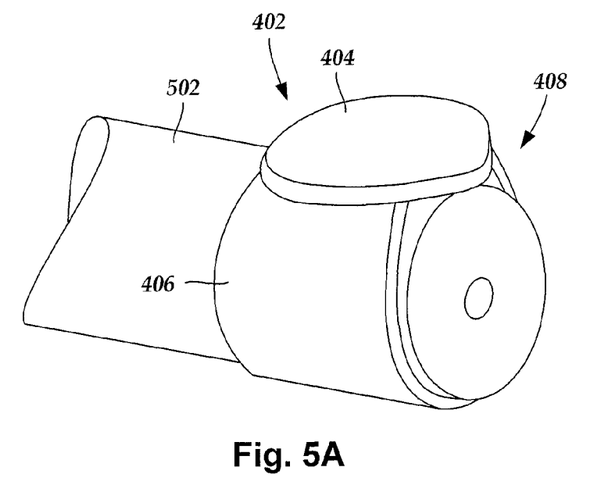
FIG. 5A is a schematic perspective view of one embodiment of a septum disposed on a portion of a connector; according to the invention.

FIG. 5A is a schematic perspective view of the septum 402 disposed on a portion of a connector 502. The septum 402 is positioned with the septum flap 404 covering the fastener aperture (not shown in FIG. 5A) The distal end 408 of the septum flap 404 overhangs the distal end 408 of the attachment cuff 406. In at least some embodiments the attachment cuff 406 is permanently attached with the underlying connector 502. In some embodiments, the septum 402 is integrally molded onto a connector 502. In other embodiments, the septum 402 is a separate structure from the connector 502 and is subsequently either permanently or removably disposed on the connector 502. In at least some embodiments, the septum 402 is thermoformed to the connector 502. In some embodiments, the attachment cuff may wrap around the connector and in other embodiments the attachment cuff may not wrap entirely around the connector.

In at least some embodiments, at least a portion of the septum flap 404 creates an interference fit with a portion of the connector 502. In at least some embodiments, at least a portion of the septum flap 404 creates an interference fit with a portion of the attachment cuff 406. In at least some embodiments, one or more of the abovementioned interference fits facilitate the prevention of fluid or tissue exposure in the region of the connector 502 beneath the septum flap 404.

Figure 5B:
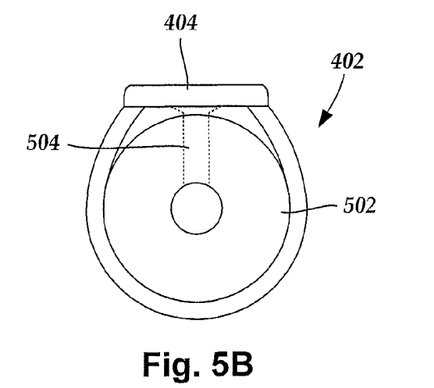
FIG. 5B is a schematic end view of one embodiment of a septum disposed on a connector; according to the invention.
Figure 5C:
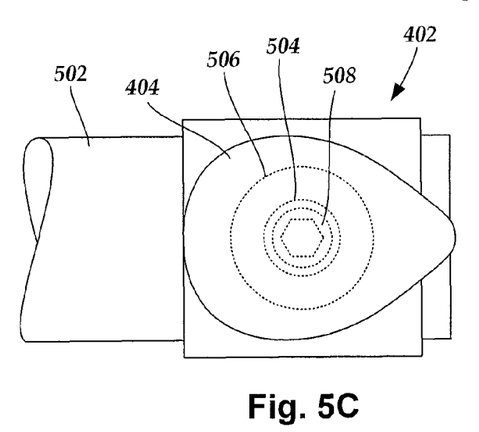
FIG. 5C is a schematic top view of one embodiment of a septum disposed on a connector; according to the invention.
Figure 5D:
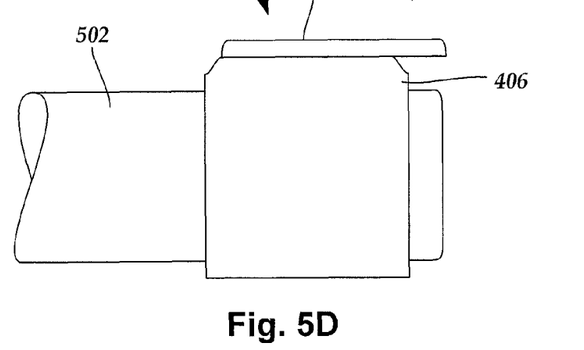
FIG. 5D is a schematic side view of one embodiment of a septum disposed on a portion of a connector; according to the invention.

FIG. 5B is a schematic end view of the septum 402 disposed on the connector 502. The septum flap 404 is covering the region (see FIG. 5C) surrounding a fastener aperture 504. FIG. 5C is a schematic top view of the septum 402 disposed on a portion of the connector 502. The septum flap 404 is covering the region 506 surrounding the fastener aperture 504. A top surface of a fastener 508 extends from the fastener aperture 504. FIG. 5D is a schematic side view of the septum 402 disposed on a portion of the connector 502. The distal end 408 of the septum flap 404 overhangs the distal end 408 of the attachment cuff 406. As discussed below, the overhanging portion of the septum flap 404 can be used to facilitate opening of the septum flap 404 and exposing the underlying fastener (see FIG. 5C).

Figure 6A:
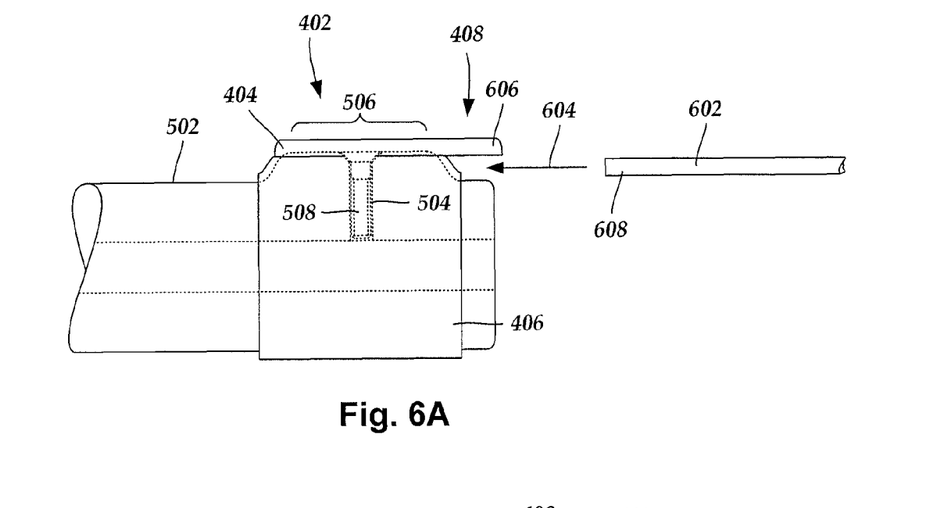
FIG. 6A is a schematic side view of one embodiment of a fastener disposed on a connector and covered by a septum, and a tool for removing the fastener; according to the invention.

FIGS. 6A-6D show one possible set of steps for using a tool to remove a fastener mated with a fastener aperture disposed in a connector housing and covered by a septum flap. In a first step, shown in FIG. 6A, the septum 402 is shown disposed on a portion of the connector 502. The attachment cuff 406 is coupled to the connector 502 so that the septum flap 404 covers the fastener 508 and the fastener aperture 504, and forms an interference fit with the region 506 surrounding the fastener aperture 504. A tool 602 is shown in FIG. 6A that can be inserted, as shown by directional arrow 604, between the attachment cuff 406 and the distal end 408 of the septum flap 404. In FIGS. 6A-6D, the fastener 508 is shown as a set screw and the tool is shown as a hex wrench configured and arranged to mate with a head of the set screw.

In at least some embodiments, an optional lead-in tab 606 is disposed at the distal end 408 of the septum flap 404. The lead-in tab 606 is configured and arranged for facilitating access to the fastener 508 with the tool 602. In at least some embodiments, the lead-in tab 606 is configured and arranged to guide a leading end 608 of the tool 602 into a position where the leading end 608 of the tool 602 can be pivoted to pry open the septum flap 404. For example, in one embodiment the lead-in tab 606 may include two or more protrusions disposed on the underside of the distal end 408 of the septum flap 404 that are configured and arranged to guide the leading end 608 of the tool 602 to a selected pivoting position between the septum flap 404 and the attachment cuff 406.

Figure 6B:
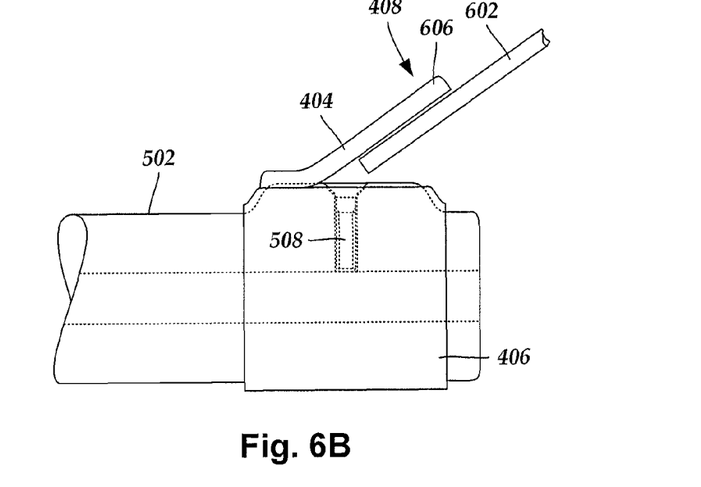
FIG. 6B is a schematic side view of one embodiment of a septum flap being pried open by a tool; according to the invention.
Figure 6C:
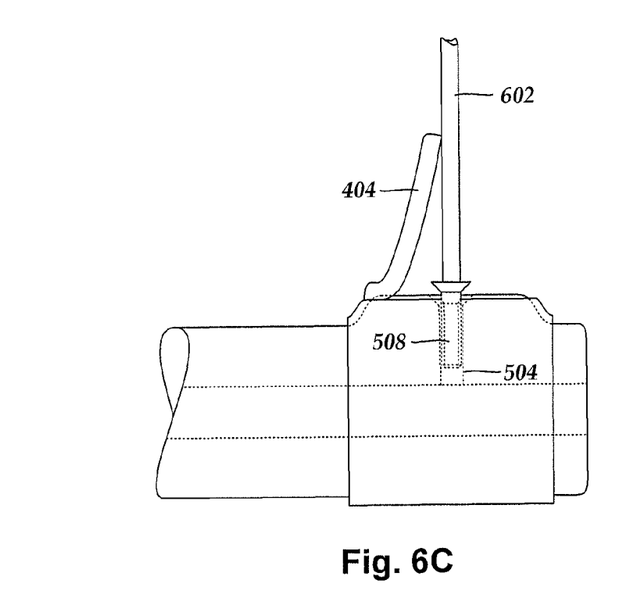
FIG. 6C is a schematic side view of one embodiment of a septum flap pried open and a fastener being removed from a connector by a tool, according to the invention.
Figure 6D:
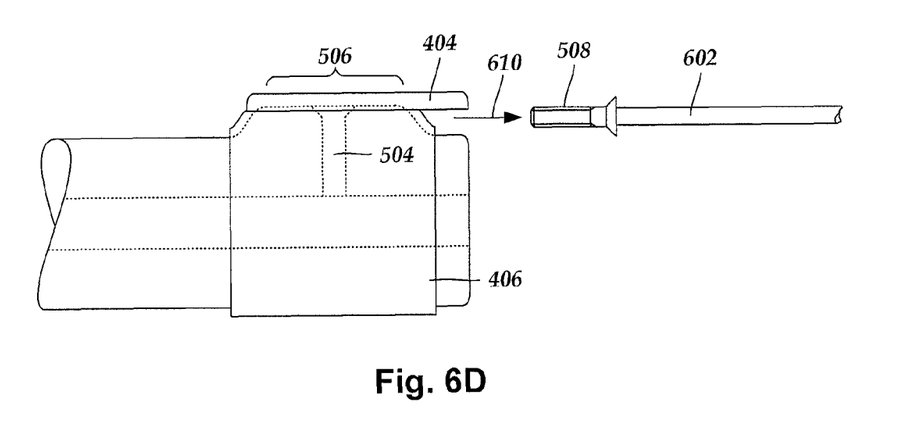
FIG. 6D is a schematic side view of one embodiment of a septum flap that is closed after a fastener is removed from a connector by a tool, according to the invention.
Figure 7A:
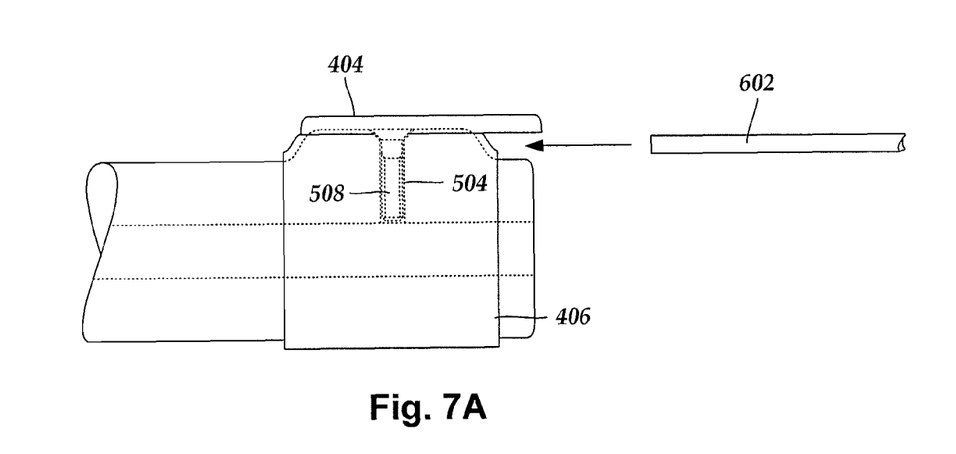
FIG. 7A is a schematic side view of a second embodiment of a fastener disposed on a connector and covered by a septum, and a tool for removing the fastener; according to the invention.
Figure 7B:
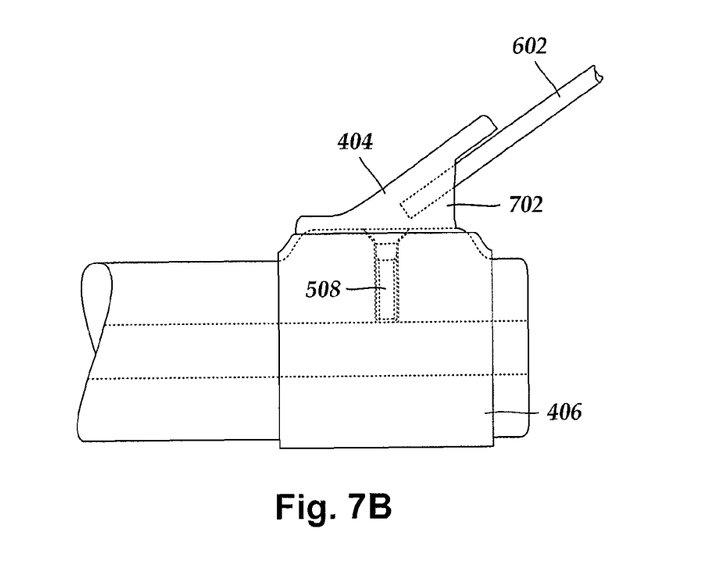
FIG. 7B is a schematic side view of a second embodiment of a septum flap being pried open by a tool; according to the invention.
Figure 7C:
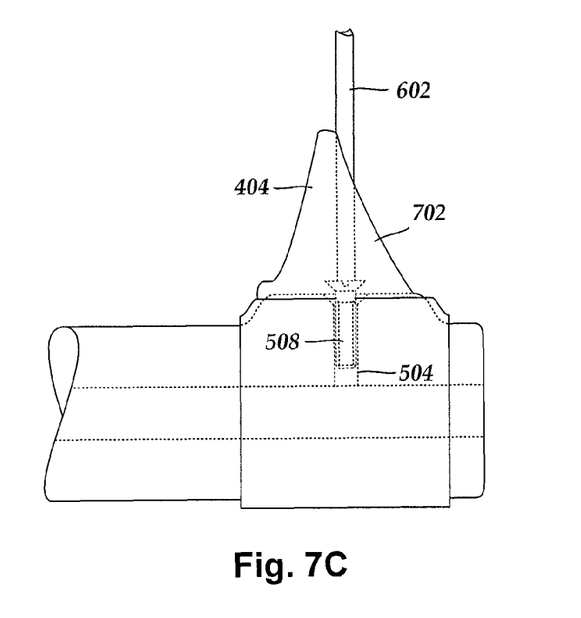
FIG. 7C is a schematic side view of a second embodiment of a septum flap pried open and a fastener being removed from a connector by a tool, according to the invention.
Figure 7D:
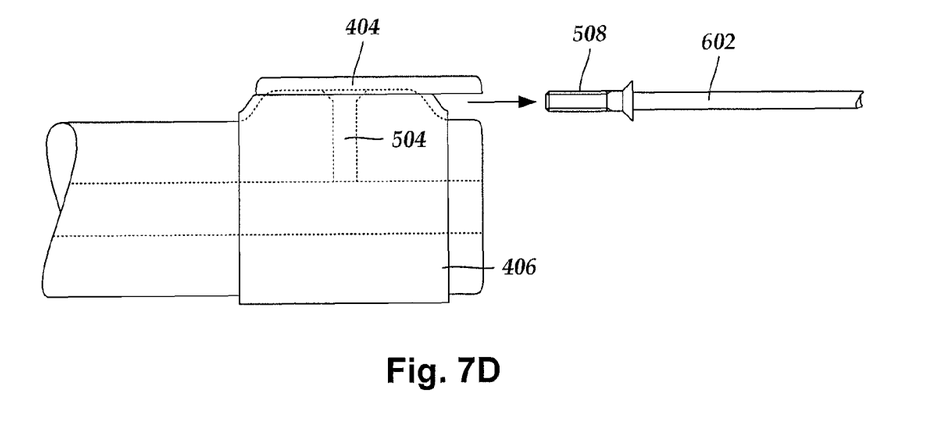
FIG. 7D is a schematic side view of a second embodiment of a septum flap that is closed after a fastener is removed from a connector by a tool, according to the invention.

In a second step, shown in FIG. 6B, the tool 602 has been inserted between the distal end 408 of the septum flap 404 and the attachment cuff 406 and the tool 602 has been pivoted to pry open the septum flap 404. The distal end 408 of the septum flap 404 is folded away from the attachment cuff 406 to expose the fastener 508. In a third step, shown in FIG. 6C, the tool 602 has been further pivoted to fold back the septum flap 404 enough to allow the tool 602 to be mated with the fastener 508 and used to partially remove the fastener 508 from the fastener aperture 504. In a fourth step, shown in FIG. 6D, the fastener 508 has been removed from the fastener aperture 504 and the fastener 508 and the tool 602 have been removed from between the septum flap 404 and the attachment cuff 406, as shown by directional arrow 606. Once the fastener 508 and the tool 602 are removed from the septum flap 404, the septum flap 404 reforms an interference fit around the region 506 surrounding the fastener aperture 504. In at least some embodiments, the steps shown in FIGS. 6A-6D may also be performed in reverse order to insert the 508 fastener into the fastener aperture 504. Additionally, in at least some embodiments, the tool 602 may also be used to access the fastener 508 in order to tighten or loosen the fastener 508 within the fastener aperture 504 without inserting or removing the fastener 508 from the fastener aperture 504. It will be understood that the complete removal of the fastener 508 may not be necessarily be needed in order to remove a coupled lead or a lead extension from the connector 502. In at least some cases, a lead or lead extension may be removed from the connector 502 by loosening the fastener 508 within the fastener aperture 504 without completely removing the fastener 508.

In at least some embodiments, a septum flap 404 may include stretchable side pieces covering one or more of sides of the septum flap 404. FIGS. 7A-7D show another possible set of steps for using the tool 602 to remove the fastener 508 mated with the fastener aperture 504 disposed in the connector housing and covered by the septum flap 404. In FIGS. 7A-7D, the septum flap includes a side piece 702 covering a side of a septum flap 404 that stretches when the tool 602 is inserted beneath the septum flap 404. In at least some embodiments, the side pieces 702 covering one or more of sides of the septum flap 404 are integral with the septum flap 404. In at least some embodiments, the side pieces 702 are also integral with the attachment cuff 406.

In at least some embodiments, the side pieces 702 of the septum flap 404 are less thick than the region 506 surrounding the fastener aperture 504. It may be an advantage to have the side pieces 702 be less thick than the region 506 surrounding the fastener aperture 504 because the side pieces 702 may need to be stretched more than the region 506 surrounding the fastener aperture 504 and the region 506 surrounding the fastener aperture 504 may be more likely to be scarred or punctured by the tool 602 during tightening/loosening of the fastener 508.

As discussed above, septa may be used to prevent undesirable interactions between bodily fluids or tissues and fastener assemblies used to secure coupled components of an electrical stimulation system, while still allowing subsequent access to covered fastener assemblies. A conventional septum includes a slit directly over top of a fastener assembly through which a tool may pass for accessing the underlying fastener. Because bodily fluids exert a pressure on the slit, the slit needs to have a thickness great enough to overcome the force of the bodily fluids in order to maintain a seal. In contrast, when a septum uses a septum flap and not a slit, the same fluid pressure directed in the same direction acts to press the septum flap more tightly against the connector.

Accordingly, the thickness of the material needed over top of a fastener assembly can be less with the septum flap 404 than with a convention slit septum. Thus, a septum with the septum flap 404 can be a smaller size than a conventional slit septum. A smaller size may be advantageous for implanting electrical stimulation systems in confined locations inside a patient. Additionally, burrowing a fastener tool through a slit formed in silicone, or similar elastomeric material, can cause damage to the walls of the slit, which may lead to degradation or loss of a seal. In contrast, using a fastener tool to pry open a septum flap formed in silicone, or similar elastomeric material, can be less harmful to the material and less likely to cause damage to the septum.

Figure 8:
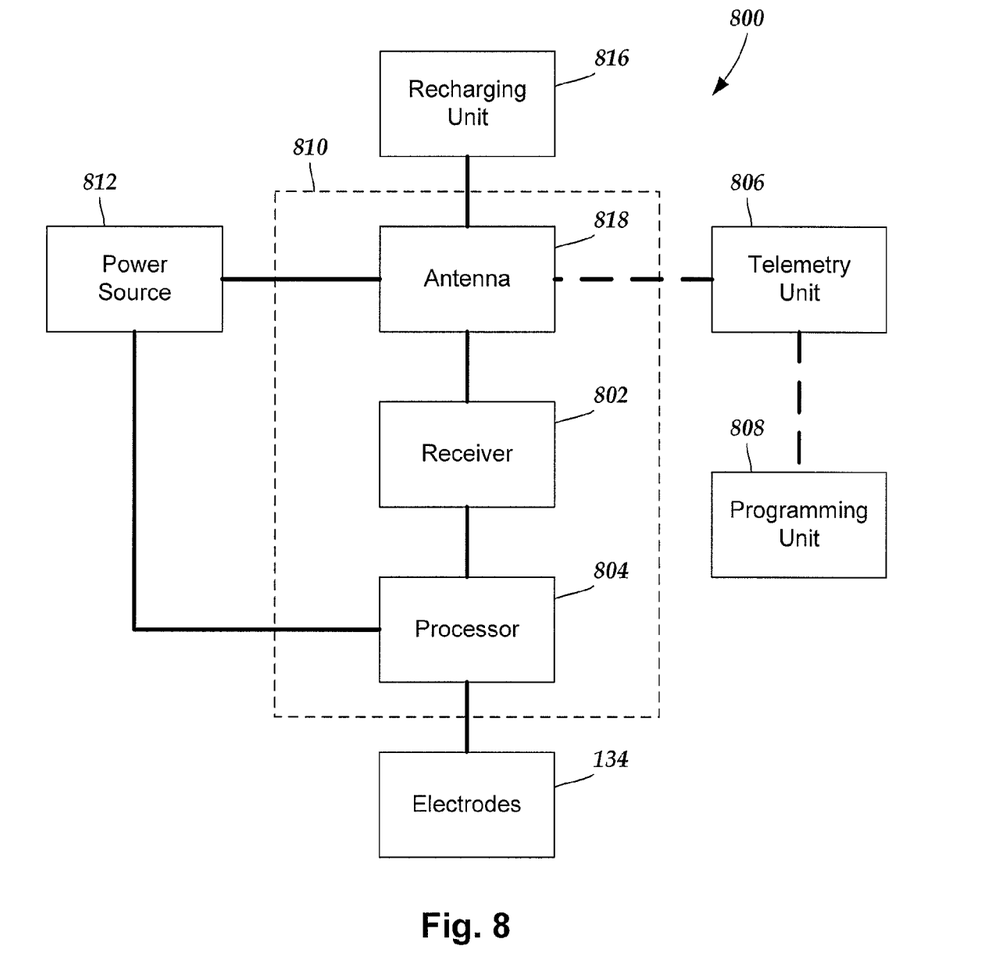
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, power source 812, antenna 818, receiver 802, and processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 may select which electrode(s) are cathodes and which electrode(s) are anodes. In some embodiments, the processor 804 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by a programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include an antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A connector for receiving an electro-stimulation lead, the connector comprising:
    a connector housing defining an opening for receiving an proximal end of the lead, the connector housing comprising a fastener aperture;
    a plurality of connector contacts disposed in the connector housing, the connector contacts configured and arranged to couple to at least one terminal disposed on the proximal end of the lead;
    a septum disposed on the connector housing, the septum comprising a septum flap and an attachment cuff, the septum flap having a distal end and a proximal end, the proximal end being attached to the attachment cuff and the distal end being unattached, the septum flap extending completely over the fastener aperture and being configured and arranged to receive a tool for lifting the distal end of the septum flap up and away from the attachment cuff, connector housing, and fastener aperture and to bend and fold the septum flap to expose the fastener aperture beneath the septum flap, the attachment cuff configured and arranged for coupling the septum flap to the connector housing;
    wherein the septum flap comprises at least one reinforcing component; and
    a fastener configured and arranged to be disposed in the fastener aperture and to be tightened against the lead to hold the lead within the connector housing.

2. The connector of claim 1, wherein the attachment cuff defines an access aperture positioned over the fastener aperture and configured and arranged for passage of the fastener and the tool through the access aperture.

3. The connector of claim 1, wherein the connector is disposed on a lead extension, the lead extension electrically coupled to a control module.

4. The connector of claim 1, wherein the connector is disposed on a control module.

5. The connector of claim 1, wherein the fastener is tightened against the lead by using the tool.

6. The connector of claim 1, wherein at least a portion of the septum flap is attached to the connector housing by an interference fit.

7. The connector of claim 1, wherein at least a portion of the septum flap is attached to the attachment cuff by an interference fit.

8. The connector of claim 1, wherein the attachment cuff is attached to the connector housing by an interference fit.

9. The connector of claim 1, wherein the septum flap comprises at least one side piece coupling the septum flap to the attachment cuff.

10. The connector of claim 1, wherein the septum is integrally molded as part of the connector housing.

11. An electrical stimulating system comprising:
    a lead having a proximal end and a distal end, the lead comprising:
        a plurality of electrodes disposed on the distal end of the lead,
        a plurality of terminals disposed on the proximal end of the lead, and
        a plurality of conductor wires extending along the lead to couple the electrodes electrically to the terminals;
    a control module configured and arranged to electrically couple to the lead, the control module comprising:
        a housing, and
        an electronic subassembly disposed in the housing; and
    a connector for receiving the lead, the connector comprising:
        a connector housing defining an opening for receiving the proximal end of the lead, the connector housing comprising a fastener aperture,
        a plurality of connector contacts disposed in the connector housing, the connector contacts configured and arranged to couple to at least one terminal disposed on the proximal end of the lead,
        a septum disposed on the connector housing, the septum having a proximal end and a distal end and comprising a septum flap and an attachment cuff, the septum flap having a distal end and a proximal end, the proximal end being attached to the attachment cuff and the distal end being unattached, the septum flap extending completely over the fastener aperture and being configured and arranged to receive a tool for lifting the distal end of the septum flap up and away from the attachment cuff, connector housing, and fastener aperture and to bend and fold the septum flap to expose the fastener aperture beneath the septum flap, the attachment cuff configured and arranged for coupling the septum flap to the connector housing,
        wherein the septum flap comprises at least one reinforcing component, and
        a fastener configured and arranged to be disposed in the fastener aperture and to be tightened against the lead to hold the lead within the connector housing.

12. The electrical stimulating system of claim 11, wherein the attachment cuff defines an access aperture positioned over the fastener aperture and configured and arranged for passage of the fastener and the tool through the access aperture.

13. The electrical stimulating system of claim 11, further including a lead extension having a proximal end and a distal end, the connector disposed on the distal end of the lead extension.

14. The electrical stimulating system of claim 13, wherein the proximal end of the lead extension is configured and arranged for insertion into another connector.

15. The electrical stimulating system of claim 11, wherein the connector is disposed on the control module.

16. The electrical stimulating system of claim 11, wherein at least a portion of the septum flap is attached to the connector housing by an interference fit.

17. The electrical stimulating system of claim 11, wherein the septum flap is attached to the attachment cuff by an interference fit.

18. A method for stimulating patient tissue, the method comprising:
   providing the electrical stimulating system of claim 11;
   implanting the lead into a patient;
   disposing the proximal end of the lead into the connector electrically coupled to the control module; and
   providing electrical signals from the control module to electrically stimulate patient tissue using at least one of the electrodes.

19. The method of claim 18, wherein the attachment cuff defines an access aperture positioned over the fastener aperture and configured and arranged for passage of the fastener and the tool through the access aperture.

* * * * *